United States Patent [19]

Dang et al.

[11] Patent Number: 4,654,176
[45] Date of Patent: Mar. 31, 1987

[54] SULPHONATED CHIRAL PHOSPHINES, THEIR PREPARATION AND THEIR USE

[75] Inventors: Tuan-Phat Dang, Lyons; Jean Jenck, Ottmarsheim; Didier Morel, Villiers sur Orge, all of France

[73] Assignee: Rhone-Poulenc Sante, Courbevoie, France

[21] Appl. No.: 635,185

[22] Filed: Jul. 27, 1984

[30] Foreign Application Priority Data

Jul. 28, 1983 [FR] France .................................. 83 12468

[51] Int. Cl.⁴ .................. C07C 143/24; C07C 143/42
[52] U.S. Cl. ............................. 260/505 R; 260/505 C; 260/512 R; 260/512 C
[58] Field of Search ........... 260/505 R, 505 C, 512 R, 260/512 C

[56] References Cited

U.S. PATENT DOCUMENTS 4,483,801  11/1984  Sabot .............................. 260/505 R
4,483,802  11/1984  Gartner et al. ................. 260/505 R

OTHER PUBLICATIONS

Chem Abstracts vol. 58 p12395a.

*Primary Examiner*—Alan Siegel
*Attorney, Agent, or Firm*—Stevens, Davis, Miller & Mosher

[57] ABSTRACT

The invention provides novel sulphonated chiral phosphines of the formula:

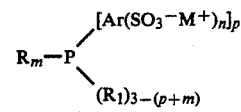

in which R represents an alkyl radical, a cycloalkyl radical optionally substituted with an alkyl radical, a cycloalkylalkyl radical optionally substituted with an alkyl radical, a phenyl, phenylalkyl, binaphthyl or binaphthylalkyl radical, in which the alkyl, cycloalkyl, phenyl and binaphthyl radicals, and the alkyl portions of the other radicals, can be substituted by a radical of general formula:

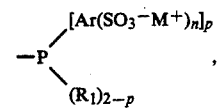

$R_1$ represents an alkyl, cycloalkyl, phenyl, or phenylalkyl radical, Ar represents a phenyl or naphthyl radical, $m^+$ represents a proton or alkali metal ion or alkaline earth metal ion, $m = 1$ or 2, $n = 0$, 1 or 2, $p = 1$ or 2, $(p+m) \leq 3$, and R and $R_1$ can be chiral or achiral. These chiral phosphines form water-soluble metal complexes useful as catalysts in asymmetric organic synthesis.

5 Claims, No Drawings

SULPHONATED CHIRAL PHOSPHINES, THEIR PREPARATION AND THEIR USE

This invention relates to asymmetric phosphines, their preparation and their use.

French Pat. No. 2,116,905 describes asymmetric phosphines which enable transition metal complexes containing optically active ligands to be obtained, their complexes being particularly useful for hydrogenation of unsaturated compounds to saturated compounds endowed with optical activity. However, these phosphines do not permit quantitative yields of only one of the isomers to be obtained.

In order to increase the selectivity of asymmetric hydrogenation of substituted acrylic acids and substituted acrylic acid esters which are precursors of amino acids, it was proposed in French Pat. No. 2,230,654 to use optically active stereoisomers of trans-1,2-bis(phosphinomethyl)cyclobutanes for the preparation of rhodium complexes. However, the use of these phosphines does not permit recycling of the catalyst.

The present invention provides certain novel sulphonated chiral phosphines from which water-soluble transition metal complexes can be obtained, which can be used for carrying out asymmetric syntheses, and which can be recycled. The new sulphonated chiral phosphines have the advantage of being water-soluble, and enable ligands of catalytic metallic complexes to be made water-soluble. It is thus possible to carry out the planned reaction in a medium comprising water and an appropriate organic solvent. Under these conditions, the reaction products are found, at the end of the reaction, in the organic phase, and the catalytic system is in the aqueous phase which can be recycled.

The present invention provides novel sulphonated chiral phosphines of the formula:

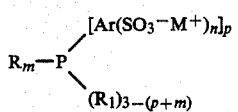
(I)

in which R represents a straight or branched alkyl radical of 1 to 12 carbon atoms, a cycloalkyl radical of 3 to 6 carbon atoms which is unsubstituted or substituted by 1 or 2 alkyl radicals of 1 to 4 carbon atoms each, a cycloalkylalkyl radical of 4 to 10 carbon atoms which is unsubstituted or substituted by an alkyl radical of 1 to 4 carbon atoms, phenyl, or phenylalkyl in which the alkyl portion contains 1 to 4 carbon atoms, binaphthyl, or binaphthylalkyl in which the alkyl contains 1 to 4 carbon atoms, the said alkyl, cycloalkyl, phenyl and binaphthyl radicals and the alkyl portions of the other radicals being optionally substituted with a further radical of the formula:

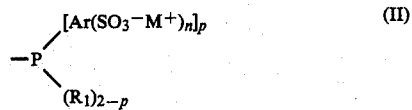
(II)

$R_1$ represents a straight or branched alkyl radical of 1 to 12 carbon atoms, a cycloalkyl radical of 3 to 6 carbon atoms, phenyl, or phenylalkyl in which the alkyl portion contains 1 to 4 carbon atoms, Ar represents phenyl or naphthyl which is unsubstituted or substituted by one or more alkyl or alkoxy radicals of 1 to 4 carbon atoms each, $M^+$ represents a proton or an ion derived from an alkali metal or an alkaline earth metal, n is 1 or 2, m is 0, 1 or 2, and p is 1 or 2, the sums of p+m being less than or equal to 3, the said radicals R and $R_1$ being chiral or achiral, such that when one of the radicals R and $R_1$ is chiral, p and m are each 1 or 2 and when the radicals R and $R_1$ are achiral, p and m are both necessarily equal to 1, and the radicals R and $R_1$ are then different so as to make the substitution on the phosphorus atom or atoms in the phosphine of the formula (I) unsymmetrical, and when m is 0, the radicals $R_1$ are different so as to make the substitution on the phosphorus atom in the phosphine of formula (I) unsymmetrical.

Of especial value are the phosphines of formula (I) in which R represents a straight or branched alkyl radical of 2 to 6 carbon atoms which is unsubstituted or substituted by a radical of formula:

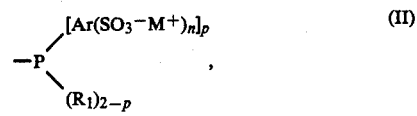
(II)

a cycloalkyl radical of 3 to 6 carbon atoms substituted by 1 or 2 alkyl radicals of 1 to 4 carbon atoms each, or a cycloalkylalkyl radical of 6 to 10 carbon atoms, in which the cycloalkyl portion contains 4 to 6 carbon atoms and is substituted by an alkyl radical of 1 to 4 carbon atoms, this alkyl radical being itself substituted with a radical of formula:

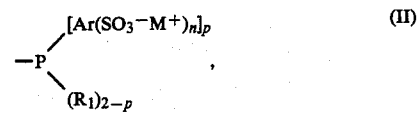
(II)

$R_1$ represents a phenyl radical, Ar represents a phenyl radical, $M^+$ represents an alkali metal ion, n is 1 or 2, m is 1, and p is 1 or 2.

According to a feature of the present invention, the novel phosphines of formula (I) are obtained by sulphonation of a phosphine of general formula:

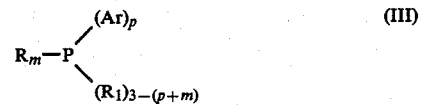
(III)

in which R, $R_1$, Ar, m and p are defined as above, one of the symbols R and $R_1$ being chiral.

The sulphonation is generally carried out by means of oleum at a temperature in the region of 20° C. It is specially advantageous to use an oleum containing 20 to 70% of sulphur trioxide.

Among the sulphonation agents which can also be used for carrying out the process according to the invention, there may be mentioned chlorosulphonic acid, the derivatives of sulphur trioxide such as sulphur trioxidedioxane mixtures, and bis-trimethylsilyl sulphate.

The sulphonation of the Ar radical of the phosphine of general formula (III) generally takes place in the meta-position.

When, in the phosphine of general formula (III), Ar and $R_1$ each represent a phenyl radical, a monosulphonation of the Ar or R radical can occur, which leads to a product of general formula (I) in which m=1, n=1 and p=1, or a disulphonation of the Ar and R radicals can occur, which leads to a product of general formula (I) in which m=1, n=1 and p=2. The sulphonation generally leads to a mixture of sulphonated phosphines which are designated as monosulphonated phosphine, disulphonated phosphine, trisulphonated diphosphine and tetrasulphonated diphosphine.

When the phosphine of general formula (III) contains 2 atoms of phosphorus, a mixture of trisulphonated diphosphine and tetrasulphonated diphosphine is formed in general, the majority being the tetrasulphonated diphosphine.

When the phosphine of general formula (III) is chiral, the sulphonation process leads to a chiral sulphonated phosphine.

When, in the phosphine of general formula (III), the radical R is racemic, the sulphonation leads to a racemic sulphonated phosphine of general formula (I) which can be resolved, for example by means of an optically active base, according to the usual techniques of resolution.

When, in the phosphine of general formula (III), the radical R is achiral and the phosphorus atom or atoms are unsymmetrically substituted, i.e. when the phosphine of general formula (III) is prochiral or racemic, the sulphonation leads to a racemic sulphonated phosphine which can be resolved, for example by means of an optically active base, according to the usual techniques of resolution.

Whatever the process used, the sulphonated phosphine obtained in acid form can be converted into an alkali metal salt through the action of a base such as an alkali metal hydroxide.

According to the process for the preparation of sulphonated phosphines of general formula (I), it is possible to obtain each of the R and S forms. Each of these forms constitutes part of the invention. However, mixtures of the chiral forms containing a major proportion of one of the forms must also be considered to constitute part of the invention.

The sulphonated chiral phosphines according to the present invention are of very special value in organic chemistry in processes of asymmetric synthesis.

More especially, the sulphonated chiral phosphines can be used to carry out asymmetric hydrogenation, hydroformylation, hydrocarboxylation, isomerisation, oligomerisation, polymerisation, oxidation, telomerisation or hydrocyanation reactions.

For example, the sulphonated chiral phosphines according to the invention, when used for the preparation of rhodium complexes, permit the asymmetric hydrogenation of substituted acrylic acids which are precursors of amino acids, or of their esters. By the terms substituted acrylic acids and substituted acrylic acid esters, there is understood the totality of the compounds having formulae which derive from that of acrylic acid and its esters by substituting at most two of the hydrogen atoms attached to ethylenic carbon atoms, in the following manner:

one of the hydrogen atoms is substituted by an amino group, which can be primary or secondary. The amino group can be substituted by an acyl group such as acetyl or benzoyl another of the hydrogen atoms attached to the ethylenic carbon atoms can be replaced by an alkyl (methyl, ethyl, isopropyl, isobutyl), cycloalkyl (cyclopentyl, cyclohexyl), aromatic (phenyl, naphthyl) or heterocyclic (furyl, pyranyl, benzopyranyl, pyrrolyl, pyridyl, indolyl) group.

Among the substituted acrylic acids and substituted acrylic acid esters which are precursors of amino acids, there can be mentioned N-acetyl-α-amino-β-phenylacrylic and N-benzoyl-α-amino-β-phenylacrylic acids in which the phenyl nucleus is optionally substituted with one or more alkyl, alkoxy or hydroxy radicals, N-acetyl-α-amino-β-indolylacrylic acid, N-benzoyl-α-amino-β-indolylacrylic acid and N-acetyl-α-amino-β-isobutylacrylic acid.

The selective asymmetric hydrogenation is performed using as catalysts rhodium complexes such as [Rh(1,5-cyclooctadiene)Cl]$_2$ ligated by the sulphonated chiral phosphines of general formula (I).

The hydrogenation is generally performed at a temperature between 20° and 100° C. and with hydrogen under a pressure of between 0.5 and 50 bars.

The rhodium complex is used in such a way that the ratio between the number of rhodium atoms present in the complex and the number of moles of the compound to be hydrogenated is between 0.1 and 0.0001.

The hydrogenation process is preferably carried out in a mixture of water and an immiscible organic solvent such as ethyl acetate.

By hydrogenation, it is therefore possible to obtain the different stereoisomers of amino acids in good yields.

Selective asymmetric hydroformylation can be carried out using as catalysts rhodium complexes ligated by sulphonated chiral phosphines of general formula (I).

Hydroformylation is generally carried out at a temperature between 20° and 150° C. and with hydrogen and carbon monoxide at a pressure of between 1 and 200 bars.

The rhodium complex is used in such a way that the ratio between the number of phosphorus atoms in the phosphine and the number of rhodium atoms present in the complex is between 2 and 100 when a monophosphine is used, and between 2 and 10 when a diphosphine is used.

The following Examples illustrate the present invention.

EXAMPLE 1

A solution of (+)-trans-1,2-bis(diphenylphosphinomethylene)cyclobutane (1 g) in sulphuric acid (66° Baumé: 2 cc) is poured into oleum containing 20% of sulphur trioxide (19 g in total) which has previously been cooled to 0° C. With the temperature maintained at 20° C. by means of a thermostatic bath, the reaction is continued for 27 hours, the progress of the reaction being monitored by $^{31}$P-NMR examination of aliquot fractions.

The reaction mixture is then poured cautiously into ice (30 g). After neutralisation by addition of 50% strength aqueous caustic soda, the sodium sulphate precipitate (59.7 g) is separated by filtration. After being cooled to 0° C., the reaction mixture is again filtered and methanol is then added. After filtration to eliminate all of the sodium sulphate, the filtrate is concentrated to dryness. Sulphonated (±)-trans-1,2-bis(diphenylphosphinomethylene)cyclobutane (0.58 g) is thus obtained.

$^{31}$P-NMR analysis, performed on the product as obtained and then oxidised by hydrogen peroxide, shows that the product obtained contains:
  tetrasulphonated diphosphine: (62%),
  trisulphonated diphosphine: (34%),
  oxides of phosphines: (4%).

The characteristics of the $^{31}$P-NMR spectrum are as follows:

(a) solvent: sulphuric acid; reference phosphoric acid:

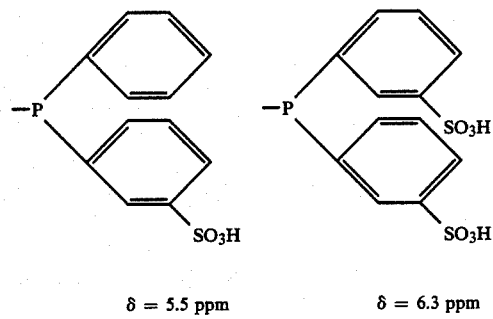

δ = 5.5 ppm   δ = 6.3 ppm (b) solvent: water; reference phosphoric acid: after oxidation by hydrogen peroxide:

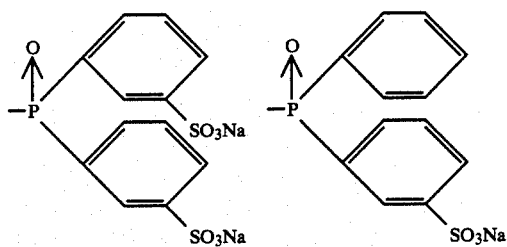

δ=37.9 ppm: tetrasulphonated diphosphine
δ=38.7 ppm: trisulphonated diphosphine.
Elementary analysis: Found: C 39.1% H 3.9% P 6.74% S 11.94% S/P=1.71 (theoretical: 2 for the tetrasulphonated phosphine; 1.5 for the trisulphonated diphosphine).

EXAMPLE 2

A solution of (−)-trans-1,2-bis(diphenylphosphinomethylene)cyclobutane (1 g) in sulphuric acid (66° Baumé: 2 cc) is poured into oleum containing 20% of sulphur trioxide (19 g in total) which has previously been cooled to 0° C. The reaction mixture is placed under a stream of nitrogen, and maintained at 22° C. for 45 hours. The reaction mixture is then poured cautiously into ice (30 g), and then neutralised by addition of 50% strength caustic soda while the temperature is maintained below 25° C.

The sodium sulphate precipitate is separated by filtration. After the filtrate is cooled to 0° C., the sodium sulphate is separated by filtration, and methanol (200 cc) is then added to the filtrate. The sodium sulphate is separated by filtration. The filtrate is concentrated to dryness. Sulphonated (−)-trans-1,2-bis(diphenylphosphinomethylene)cyclobutane is thus obtained (2.32 g).

$^{31}$P-NMR analysis shows that the product obtained contains oxides of phosphines (7%), and sulphonated phosphine (93%) consisting of tetra(metasulphonated)diphosphine (67%) and tri(metasulphonated)diphosphine (33%).

The rotatory power is: $[\alpha]_D=11.6°$ (C=0.52, water).

EXAMPLE 3

A solution of (−)-(2S,3S)-bis(diphenylphosphino)butane (0.8 g) in sulphuric acid (66° Baumé: 1.6 cc) is poured into oleum containing 20% of sulphur trioxide (16 g in total) which has previously been cooled to 0° C. The reaction mixture is stirred for 28 hours at 22° C. After the mixture is cooled to 0° C., ice (25 g) is added cautiously while the temperature is maintained below 15° C. The reaction mixture is then neutralised (pH=7) by addition of 50% strength caustic soda. The sodium sulphate is separated by filtration. After the filtrate is cooled to 0° C., the sodium sulphate is separated by filtration and then methanol (60 cc) is added to the filtrate. The sodium sulphate precipitated is separated by filtration. The filtrate is concentrated to dryness. Sulphonated (−)-(2S,3S)-bis(diphenylphosphino)butane (1.6 g; fraction A) is thus obtained.

The last two precipitates of sodium sulphate are combined and washed with methanol (200 cc). After filtration, the methanolic filtrate is evaporated to dryness. A second fraction of sulphonated (−)-(2S,3S)-bis(diphenylphosphino)butane (0.4 g; fraction B) is thus obtained.

Iodometric determination shows that fraction A contains 18% of sulphonated phosphine and fraction B contains 75% of sulphonated phosphine (reckoned as tetrasulphonated diphosphine).

$^{31}$P-NMR analysis shows that, for fraction B, the ratio phosphines/oxides of phosphines=76/24.

Elementary analysis of fraction B shows that the ratio S/P=1.55.

EXAMPLE 4

To a solution of (−)-(2S,3S)-bis(diphenylphosphino)butane (0.7 g) in 98.5% strength sulphuric acid (4 cc) is added oleum containing 65% of sulphur trioxide (3.5 cc total volume). The reaction mixture is stirred for 22 hours at 22° C. After the mixture is cooled to −5° C., ice (20 g) is added in small portions. While the temperature is maintained below 10° C., the reaction mixture is neutralised by addition of 50% strength caustic soda. The precipitate of sodium sulphate is separated by filtration. After addition of methanol to the filtrate, sodium sulphate is again separated by filtration and the filtrate is then concentrated to dryness. Sulphonated (−)-(2S,3S)-bis(diphenylphosphino)butane (0.985 g) is thus obtained.

$^{31}$P NMR analysis (solvent: water; reference phosphoric acid) shows that there are oxides of phosphines (10% in total: 6% δ=43.5 ppm; 4% δ=44.3 ppm) and sulphonated phosphines (90% in total: 72% δ=−9.7 ppm; 15% δ=−8.9 ppm; and 3% δ=−7.3 ppm).

Elementary analysis indicates a ratio S/P=1.45.
Rotatory power: $[\alpha]_D=-98.5°$ (C=0.965, water).

EXAMPLE 5

A solution of neomenthyldiphenylphosphine (0.5 g) in 98% strength sulphuric acid (2 cc) is added to oleum containing 20% of sulphur trioxide (10 cc total volume). The mixture is stirred for 2 hours at 22° C., ice (30 g) is then added cautiously in small portions, and the mixture is neutralised (pH=7) by addition of 50% strength caustic soda while the temperature is maintained below 15° C. The sodium sulphate is separated by filtration. Methanol is added to the filtrate, and the sodium sulphate is then again separated by filtration. After the filtrate is concentrated to dryness, sulphonated neomenthyldiphenylphosphine (1.08 g) is obtained.

$^{31}$P-NMR analysis shows that the product contains oxides of phosphines [43% in total: δ=+20.8 ppm (4.5%); δ=+33.6 ppm (7.5%); δ=34.4 ppm (31%)] and sulphonated phosphine [57% in total: δ= −15.4 ppm (31%); δ= −14.7 ppm (26%)] corresponding to the two diastereoisomers.

Rotatory power: $[\alpha]_D = +53°$ (C=0.47, methanol).

EXAMPLE 6

Under an atmosphere of nitrogen, [Rh(1,5-cyclooctadiene)Cl]₂ (25 mg; 0.1 milligram-atom of rhodium) and sulphonated diphosphine (prepared in Example 1: 112 mg or 0.11 mmole) is dissolved in water (10 cc). This solution is injected into a hydrogenation reactor containing a suspension of α-acetamidocinnamic acid (4.1 g or 20 mmoles) in distilled ethyl acetate (20 cc).

The hydrogenation is performed with hydrogen under a pressure of 1 bar at a temperature in the region of 20° C. The hydrogenation lasts 1 hours 40 minutes. The starting substrate becomes soluble as the hydrogenation proceeds. The organic phase which contains the N-acetylphenylalanine is separated by decantation. After concentration to dryness, N-acetylphenylalanine (3.9 g) is obtained. The reactor containing the aqueous solution of the catalyst is recharged with α-acetamidocinnamic acid (20 mmoles), and the hydrogenation is started again. The procedure is repeated 4 times, similar results being obtained.

EXAMPLE 7

Under an atmosphere of nitrogen, [Rh(1,5-cyclooctadiene)Cl]₂ (26.2 mg; 0.106 milligram-atom of rhodium) and sulphonated phosphine (prepared in Example 2: 175 mg or 0.13 mmole) are dissolved in water (10 cc). This solution is injected into a hydrogenation reactor containing a suspension of Z-α-acetamidocinnamic acid (4.1 g) in ethyl acetate (20 cc).

The hydrogenation is performed with hydrogen under a pressure of 1 bar at a temperature in the region of 20° C. After 50 minutes' reaction, the theoretical quantity of hydrogen is absorbed. The organic phase is separated by decantation, and is then concentrated to dryness. N-acetylphenylalanine (3.9 g) is thus obtained, its rotatory power being:

$[\alpha]_D = +23.3°$ (C=1, ethanol).

The product obtained has an optical purity of 51%.

EXAMPLE 8

Under an atmosphere of nitrogen, [Rh(1,5-cyclooctadiene)Cl]₂ (9.8 mg; 0.04 milligram-atom of rhodium) and sulphonated diphosphine (prepared in Example 2: 71 mg or 1.04 mmole) are dissolved in water (10 cc). This solution is injected into a hydrogenation reactor containing methyl Z-α-acetamidocinnamate (4.38 g or 20 mmoles) in ethyl acetate (20 cc).

The hydrogenation is performed with hydrogen under a pressure of 1 bar at a temperature in the region of 20° C. The hydrogenation lasts 70 minutes.

The organic phase is separated by decantation and then concentrated to dryness. N-acetylphenylalanine methyl ester (3.8 g) is thus obtained, its rotatory power being:

$[\alpha]_D = -20.2°$ (C=1, chloroform).

The product obtained has an optical purity of 20%, the rotatory power of the reference N-acetylphenylalanine methyl ester being $[\alpha]_D = 101.3°$ (chloroform) according to J. Organomet. Chem., 121, 249 (1976).

EXAMPLE 9

In a glass ampoule, there are introduced methyl α-acetamidocinnamate (788 mg or 3.6 mmoles), [Rh(1,5-cyclooctadiene)Cl]₂ (8.8 mg; 0.036 milligram-atom of rhodium) and sulphonated diphosphine (fraction B prepared in Example 3: 53 mg). After the system is purged with nitrogen, ethyl acetate (10 cc) and water (5 cc) are injected. Without being stoppered, the glass ampoule is introduced into an autoclave which is then purged with a stream of hydrogen. The autoclave is stirred for 17 hours with hydrogen present at a pressure of 10 bars. After the system is purged with a stream of nitrogen, the upper organic phase is withdrawn and then concentrated to dryness. N-Acetylphenylalanine methyl ester (0.58 g) is thus obtained pure (according to vapour phase chromatographic analysis), its rotatory power being:

$[\alpha]_D = -80.8°$ (C=1, chloroform).

The product obtained has an optical purity of 79.8%.

The glass ampoule is recharged with methyl α-acetamidocinnamate (788 mg) and ethyl acetate (10 cc). After being purged with hydrogen, the autoclave is stirred for 17 hours with hydrogen present at a pressure of 10 bars. After the system is purged with a stream of nitrogen, the upper organic phase is withdrawn and then concentrated to dryness. N-Acetylphenylalanine methyl ester (0.55 g) is thus obtained pure (according to vapour phase chromatographic analysis), its rotatory power being:

$[\alpha]_D = -86.3°$ (C=1, chloroform).

The product obtained has an optical purity of 85%.

A second recycling of the catalyst is performed under the conditions described above, but introducing methyl α-acetamidocinnamate (1.6 g) and ethyl acetate (10 cc). Pure N-acetylphenylalanine methyl ester (1.33 g) is thus obtained with a conversion of 100%, its rotatory power being:

$[\alpha]_D = -87.3°$ (C=1, chloroform).

The product obtained has an optical purity of 86%.

EXAMPLE 10

In a glass ampoule, there are introduced α-acetamidocinnamic acid (740 mg or 3.6 mmoles), [Rh(1,5-cyclooctadiene)Cl]₂ (8 mg; 0.036 milligram-atom of rhodium), sulphonated diphosphine (prepared in Example 4: 52 mg) and silver borofluorate (7 mg). After the system is purged with a stream of nitrogen, ethyl acetate (10 cc) and water (5 cc) are injected.

Without being stoppered the glass ampoule is introduced into an autoclave, which is then purged with a stream of hydrogen. The autoclave is stirred for 17 hours with hydrogen present at a pressure of 10 bars. After the system is purged with a stream of nitrogen, the upper organic phase is withdrawn and then concentrated to dryness. N-Acetylphenylalanine (0.71 g) is thus obtained, its rotatory power being:

$[\alpha]_D = -38.2°$ (C=1, ethanol).

The product obtained has an optical purity of 83%.

We claim:

1. An optically active sulphonated chiral phosphine of the formula:

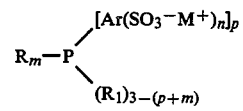

in which R represents a straight or branched alkyl radical of 1 to 12 carbon atoms, a cycloalkyl radical of 3 to 6 carbon atoms which is unsubstituted or substituted by 1 or 2 alkyl radicals each containing 1 to 4 carbon atoms, a cycloalkylalkyl radical of 4 to 10 carbon atoms which is unsubstituted or substituted by an alkyl radical of 1 to 4 carbon atoms, phenyl, a phenylalkyl radical in which the alkyl portion contains 1 to 4 carbon atoms, or a binaphthyl or binaphthylalkyl radical in which the alkyl portion contains 1 to 4 carbon atoms, the said alkyl, cycloalkyl, phenyl and binaphthyl radicals and the alkyl portions of the other radicals being optionally substituted with a further radical of the formula:

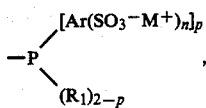

$R_1$ represents a straight or branched alkyl radical of 1 to 12 carbon atoms, a cycloalkyl radical of 3 to 6 carbon atoms, phenyl, or a phenylalkyl radical in which the alkyl portion contains 1 to 4 carbon atoms; Ar represents a phenyl or naphthyl radical which is unsubstituted or substituted by one or more alkyl or alkoxy radicals of 1 to 4 carbon atoms;

$M^+$ represents a proton or an ion derived from an alkali metal or an alkaline earth metal;

n represents 1 or 2, m represents 0, 1 or 2; and p represents 1 or 2, the sum of p+m being less than or equal to 3;

the said radicals R and $R_1$ being chiral or achiral, such that when one of the radicals R and $R_1$ is chiral, p and m are each equal to 1 or 2, and when the radicals R and $R_1$ are achiral, p and m are both necessarily equal to 1, and the radicals R and $R_1$ are then different so as to make the substitution on the phosphorus atom or atoms in the phosphine of formula (I) unsymmetrical, and when m is equal to 0, the radicals $R_1$ are different so as to make the substitution on the phosphorus atom in the phosphine of formula (I) unsymmetrical.

2. An optically active sulphonated chiral phosphine as claimed in claim 1 in which R represents a straight or branched alkyl radical of 2 to 6 carbon atoms which is unsubstituted or substituted by a radical of formula:

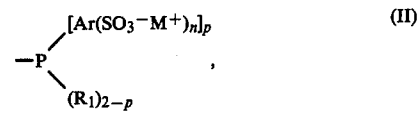

a cycloalkyl radical of 3 to 6 carbon atoms substituted by 1 or 2 alkyl radicals of 1 to 4 carbon atoms each, or a cycloalkylalkyl radical of 6 to 10 carbon atoms, in which the cycloalkyl portion contains 4 to 6 carbon atoms and is substituted by an alkyl radical of 1 to 4 carbon atoms, this alkyl radical being itself substituted with a radical of formula:

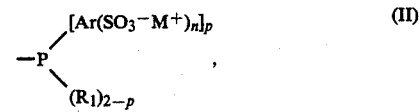

$R_1$ represents a phenyl radical, Ar represents a phenyl radical, $M^+$ represents an alkali metal ion, n is 1 or 2, m is 1 and p is 1 or 2.

3. An optically active sulphonated chiral phosphine as claimed in claim 1 which is sulphonated (−)-trans-1,2-bis(diphenylphosphinomethylene)cyclobutane.

4. An optically active sulphonated chiral phosphine as claimed in claim 1 which is sulphonated (−)-(2S,3S)-bis(diphenylphosphino)-butane.

5. An optically active sulphonated chiral phosphine as claimed in claim 1 which is sulphonated neomenthyl diphenylphosphine.

* * * * *